US006635871B2

United States Patent
Xu et al.

(10) Patent No.: US 6,635,871 B2
(45) Date of Patent: Oct. 21, 2003

(54) POSITRON LIFETIME SPECTROMETER USING A DC POSITRON BEAM

(75) Inventors: Jun Xu, Knoxville, TN (US); Jeremy Moxom, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 214 days.

(21) Appl. No.: 09/894,776

(22) Filed: Jun. 28, 2001

(65) Prior Publication Data

US 2003/0001092 A1 Jan. 2, 2003

(51) Int. Cl.[7] ............................. G21K 7/00; G21N 23/00
(52) U.S. Cl. ......................................... 250/306; 250/309
(58) Field of Search .................................. 250/306, 307, 250/308, 309

(56) References Cited

U.S. PATENT DOCUMENTS 5,200,619 A * 4/1993 Asoka Kumar et al. ..... 250/307

OTHER PUBLICATIONS

1) D. Schodlbauer, P. Sperr, G. Kogel and W. Triftshauser, "A Pulsed Positron Beam for Lifetime Studies", Positron Annihilation, eds P.C. Jain, R.M. Singru and K.P. Gopinathan, (World Scientific, Singapore, 1985) p. 957–959.

2) R. Suzuki, T. Mikado, H. Ohgaki, M. Chiwaki and T. Yamazaki, "An Intense Pulsed Positron Beam and its Applications", eds E. Ottewitte and A.H. Weiss, AIP Conference Proceedings 303, (AIP Press, New York, 1992) p. 526–534.

3) K.G. Lynn, W.E. Frieze and P.J. Schultz, "Measurement of the Position Surface–State Lifetime for Al", Phys. Rev. Lett. 52, No. 13, 1137–1140 (1984).

4) S. Szpala, Defect Identification Using Analysis of Core–Electrons Contribution to Doppler Broadening of the Positron Annihilation Line and Measurements of Positron Lifetime, Ph.D. Dissertation, The City University of New York, 1999.

* cited by examiner

Primary Examiner—Huan Tran
(74) Attorney, Agent, or Firm—James M. Spicer

(57) ABSTRACT

An entrance grid is positioned in the incident beam path of a DC beam positron lifetime spectrometer. The electrical potential difference between the sample and the entrance grid provides simultaneous acceleration of both the primary positrons and the secondary electrons. The result is a reduction in the time spread induced by the energy distribution of the secondary electrons. In addition, the sample, sample holder, entrance grid, and entrance face of the multichannel plate electron detector assembly are made parallel to each other, and are arranged at a tilt angle to the axis of the positron beam to effectively separate the path of the secondary electrons from the path of the incident positrons.

4 Claims, 4 Drawing Sheets

POSITRON LIFETIME SPECTROMETER USING A DC POSITRON BEAM

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

BACKGROUND OF THE INVENTION

1. Field of the Invention

This invention relates to a positron lifetime spectrometer based on a DC positron beam. More particularly, it relates to a positron lifetime spectrometer having a wide valid time range that results from a uniquely straightforward spectrometer design and an improved time resolution brought about by simultaneously accelerating both the primary positrons and the secondary electrons produced by the spectrometer.

2. Background Information

As materials are engineered and manipulated at nanometer scale, defects in those materials become very important because they can drastically alter the material properties and device functionality. Conventional techniques such as cross section transmission electron microscopy (XTEM) and neutron scattering are limited by their selectivity and sensitivity to micro open-volume defects. Positron lifetime spectroscopy (PLS), on the other hand, is fundamentally sensitive to open-volume defects because positrons are preferentially trapped at defect sites. In addition, positron spectroscopy is a nondestructive technique.

When positrons enter a solid, they are trapped in vacancies, vacancy clusters and voids because these sites provide local minima in the potential energy. The trapped positrons annihilate with the electrons of surrounding atoms, generating gamma ($\gamma$) radiation that is used to signature defects. By varying the energy of the incident positrons, the characterization of defects as a function of depth in the material can be carried out.

In one current method, positron lifetime spectroscopy based on an isotope positron source detects size and concentration of defects in bulk materials. Isotope-based PLS, however, is a non-beam type of PLS that cannot characterize defects in thin films or in their substrate interfaces because positrons generated by an isotope yield a broad energy distribution varying from 0 to 500 keV.

In recent years, positron lifetime spectroscopy in conjunction with either a variable energy pulsed positron beam or a variable energy DC positron beam has been found to be increasingly useful for characterizing defects in thin films and their substrate interfaces as semiconductor and optical devices are made in nanometer scale.

The measures of performance of a positron lifetime spectrometer include 1) the time range over which a sum of exponential decay functions are fitted to the lifetime spectrum without interference from spurious structures, i.e., "ghost" peaks; 2) the time resolution, defined as the full width of half-maximum (FWHM) of a single time peak; and 3) the signal-to-noise ratio.

Schodlbauer et al of the Institut fur Nukleare Festkorperphysik of Germany has conducted positron lifetime spectroscopy using a pulsed positron beam. That spectrometer chops a DC positron beam into pulses, then bunches the pulses into narrow pulses. An advantage of the spectrometer system is its ability to generate very narrow pulses. A disadvantage is that the system requires the construction of a buncher, which is very expensive. Another disadvantage is the loss of many positrons during the chopping and bunching processes.

Suzuki et al of the Electrotechnical Laboratory in Japan has a different pulsed beam positron lifetime spectrometer. It employs a longitudinal rather than transversal chopper, and it also utilizes a positron buncher. The spectrometer reduces positron loss during the chopping process. However, its disadvantages are the same as those of the Munich spectrometer.

Closer to the present invention is a positron lifetime spectrometer originated by Lynn et al at Brookhaven National Laboratory, and revised by Szpala. Lynn's original spectrometer is based on a DC positron beam, and it uses the secondary electrons generated by the primary positrons as a time signal. The revised spectrometer relies on an additional electrode, called a retarding grid, to accelerate the electrons. However, the electrical potential applied to the retarding grid (+600 V) decelerates the incoming positrons. Therefore, the potential cannot be too high (<600 V) or it interferes with the incoming positrons. This constraint limits the reduction of the time spread induced by the electron energy distribution. The spectrometer also uses an ExB field for separating the electron flight path from that of the primary positrons.

The valid time range of the Szpala revised spectrometer is 0–3 nsec. After that, there are some "ghost" structures, possibly due to the contributions from back-scattered positrons annihilating in the ExB separator. The spectrometer has a time resolution of 475 psec. The signal-to-noise ratio of the Szpala spectrometer is about 100 in its valid time range. If the "ghost" structures are discounted, the signal-to-noise ratio of the Szpala spectrometer is much higher.

The present invention is a positron lifetime spectrometer based on a DC positron beam. It is useful in studies of advanced materials such as characterizing pore structures in thin films. It uses the secondary electrons generated by bombardment of the primary positrons on the sample to start the positron lifetime clock, and uses the detection signal of the annihilation gamma ($\gamma$) radiation to stop the clock. The spectrometer is of a uniquely simple construction that utilizes the sample potential to simultaneously accelerate both the primary (incident) positrons and the secondary electrons. This construction provides the important benefit of reducing the time spread induced by the energy distribution of the secondary electrons, while also providing a spectrometer operating in a very straightforward manner. In an additional construction feature of the invention, the path of the secondary electrons is separated from that of the incoming positrons. This is achieved by tilting the beam acceleration direction away from the original positron direction, i.e., the direction of the incoming positron beam.

REFERENCES

1) D. Schodlbauer, P. Sperr, G. Kogel and W. Triftshauser, "A Pulsed Positron Beam for Lifetime Studies", Positron Annihilation, eds P. C. Jain, R. M. Singru and K. P. Gopinathan, (World Scientific, Singapore, 1985) p.957–959.
2) R. Suzuki, T. Mikado, H. Ohgaki, M. Chiwaki and T. Yamazaki, "An Intense Pulsed Positron Beam and its Applications", eds E. Ottewitte and A. H. Weiss, AIP Conference Proceedings 303, (AIP Press, New York, 1992) p.526–534.
3) K. G. Lynn, W. E. Frieze and P. J. Schultz, "Measurement of the Positron Surface-State Lifetime for Al", Phys. Rev. Lett. 52, No. 13, 1137–1140 (1984)

4) S. Szpala, "Defect Identification Using Analysis of Core-Electrons Contribution to Doppler Broadening of the Positron Annihilation Line and Measurements of Positron Lifetime, Ph.D. Dissertation, The City University of New York, 1999.

BRIEF SUMMARY OF THE INVENTION

A spectrometer for positron lifetime characterization of defects in materials such as thin films, film substrate interfaces, or their substrates is described. A DC positron beam is directed onto a sample surface to produce annihilation gamma radiation and secondary electrons from the sample, the annihilation gamma radiation is detected by a gamma detector, and the secondary electrons are detected by an electron detector. To these common positron lifetime spectrometer components, a single entrance grid is added. The entrance grid is situated in the incident positron beam, is positioned parallel to the sample surface, and is arranged to have a higher electrical potential than the sample potential. In addition, the entrance face of the electron detector assembly is situated parallel to the entrance grid, the entrance face of the electron detector assembly is arranged to have the same potential as the entrance grid, and the sample surface, entrance grid, and entrance face of the electron detector assembly are disposed at a tilt angle to the incident DC positron beam.

DETAILED DESCRIPTION OF THE INVENTION

Figure 1:
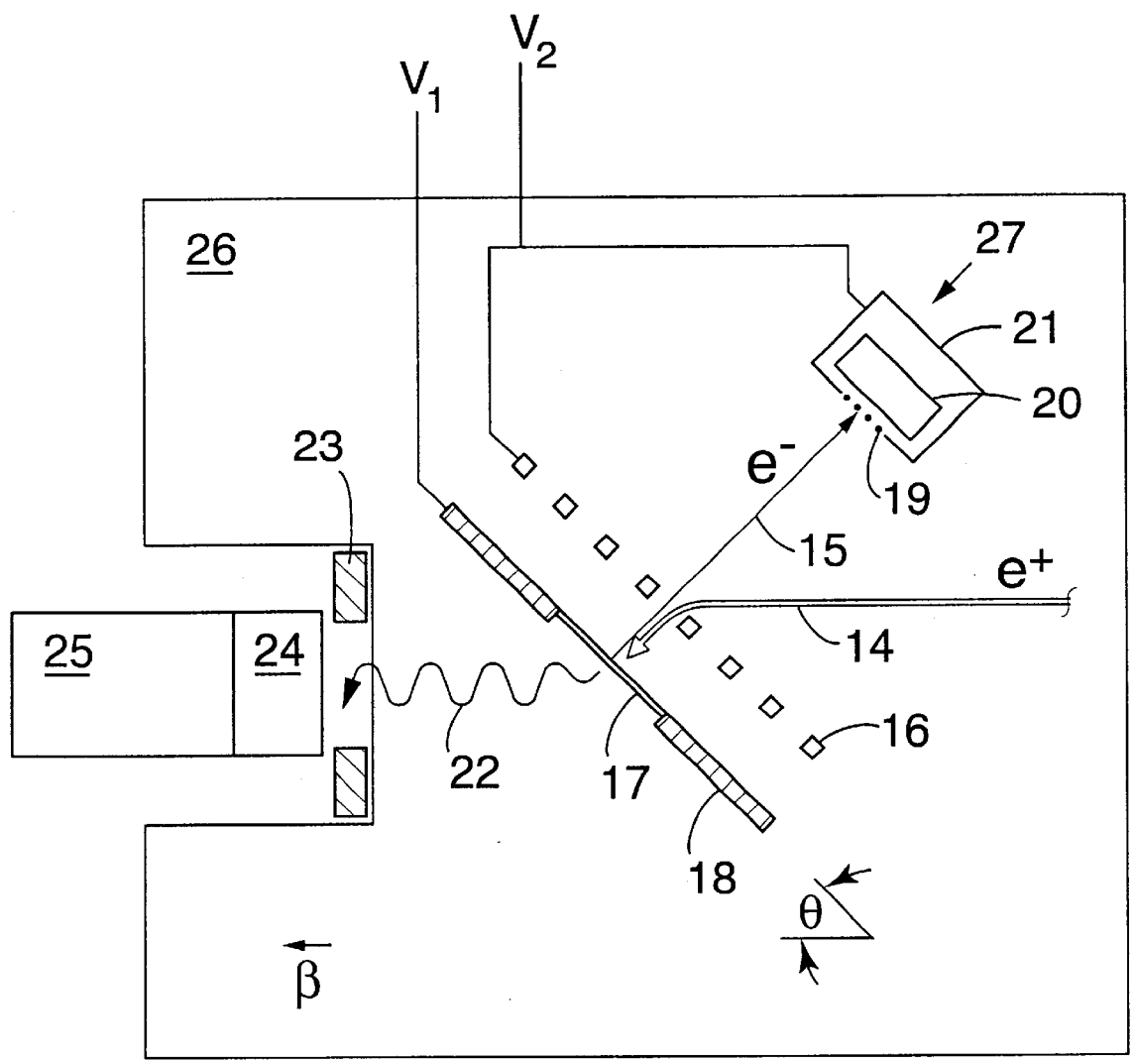
FIG. 1 illustrates a DC beam positron lifetime spectrometer according to the invention.

In FIG. 1, a DC positron beam 14 is generated in a vacuum chamber 26. The positrons can be produced by moderation of positrons emitted from radioactive isotopes, or they can be produced as a positron beam from an electron linear accelerator, for example. More particularly, the beam 14 is made up of positrons having a monochromatic energy of, for example, 10 eV. The positrons move in approximately the same direction due to the presence of a magnetic field B. The positrons 14 strike the sample 17, which may be a thin solid film, a film substrate interface, or a substrate, for example. The sample 17 is mounted in a metallic sample holder 18 that can be maintained at a selected electrical potential. The sample is thus maintained at the sample holder potential. When the mono-energetic positrons 14 bombard the sample 17, secondary electrons 15 are ejected from the sample. The detection of the secondary electrons 15 by a shielded multi-channel plate (MCP) electron detector 20 is used to generate the start signal for the positron lifetime spectrometer. The MCP detector 20 is typically mounted in an electrically shielded housing 21 that is maintained at a potential $V_2$. The. MCP electron detector 20 and housing 21 comprise a MCP electron detector assembly 27.

The stop signal of the spectrometer is derived from the detection of the gamma radiation 22 from the positron annihilations. This is accomplished with a scintillation detector 24, such as a $BaF_2$ detector, for example, and an associated PM tube 25. The scintillation detector 24 is shielded by a collimator 23 that is used to align the detector 24 with the sample 17. Measurements of the number of annihilation events as a function of the difference between the start time and the stop time are then used to construct the positron lifetime spectrum.

The above described elements and functions are considered to be known in the art. The present invention has to do with providing a means for simultaneously accelerating both the incoming positrons and the secondary electrons by a single potential difference between the sample and an entrance grid in front of the sample. The invention also separates the path of the secondary electrons from that of the positrons by tilting the acceleration direction away from the incident positron direction.

More particularly, as shown in FIG. 1, the incident positron beam 14 is initially passed through an entrance grid 16 that has been carefully positioned in front of the sample 17. The incident positrons 14 are accelerated to the desired implantation energy by the potential $V_1$ applied to the sample holder 18. The potential $V_1$ is lower than the potential $V_2$ applied to the entrance grid 16. The potential difference $V_1-V_2$ accelerates the secondary electrons 15 away from the sample 17 toward the multi-channel-plate (MCP) electron detector 20. The entrance face 19 of the electron detector assembly 27 is positioned parallel to the sample 17.

The energy of the secondary electrons 15 is distributed in a range between approximately 0 and 40 eV, depending on the sample material. For example, a 10 eV spread of energy would cause hundreds of psec worse time resolution for 600 V acceleration. With the acceleration of electrons provided by this invention, for example 10 kV, the time spread induced by the 10 eV electron energy uncertainty is reduced to less than 100 psec. Another benefit of the simultaneous acceleration method is that no additional bias is needed for accelerating the electrons, which would decelerate the incoming positrons.

Another advantage of the simultaneous acceleration (dual acceleration) method is less contribution of backscattering positrons since the amount of apparatus in front of sample is minimized. Because of this advantage, no abnormal or "ghost" structures are produced.

FIG. 1 also illustrates a second major aspect of the invention, the separation of the secondary electron path from the path of the incoming positrons. The sample 17, sample holder 18, entrance grid 16, and entrance face 19 of the multichannel plate electron detector assembly 27 are made to be parallel to each other, and are arranged at a tilt angle θ to the axis of the positron beam 14. Because of the potential difference $V_1-V_2$, the incoming positrons 14 strike the sample 17 approximately normal to its surface. This is shown in more detail in the computer simulation graph of FIG. 2.

The tilt angle θ of the sample 17, sample holder 18, entrance grid 16, and entrance face 19 of the multichannel plate electron detector assembly 27 effectively separates the path of the secondary electrons 15 from the path of the incident positrons 14. The tilt angle is selected such that the electron detector assembly 27 does not block the incoming positron beam 14. An angle of about 45 degrees was found to be practical in some test embodiments of the invention.

A large number of positron beam characterization facilities have found it useful to maintain the sample at ground or positive electrical potential. In our invention, $V_1$ can be maintained at 0 V or at a positive potential. The potential $V_2$ would still be maintained at a higher potential than $V_1$.

Figure 2:
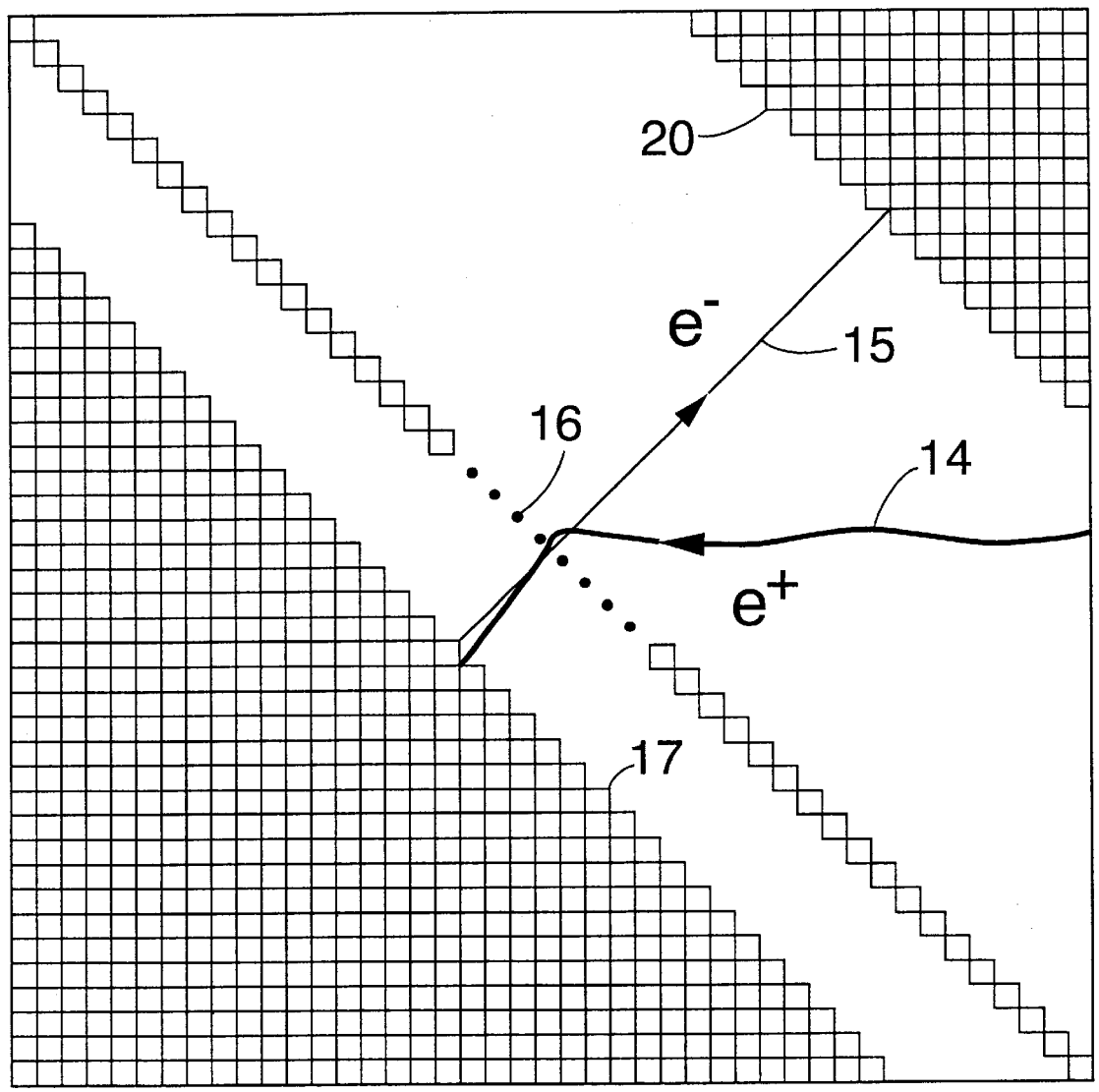
FIG. 2 is a computer simulation graph of trajectories of both 10-eV incident positrons and secondary electrons with −10 kV applied to the sample, a 50 gauss magnetic field, and a tilt angle θ of 45°.

FIG. 2 Computer Simulation Graph

FIG. 2 is a computer simulation graph illustrating the trajectories of both the incident positrons 14 and the secondary electrons 15 in the spectrometer. In this calculation, the incident positrons have an energy of 10 eV. The energy spread of secondary electrons initially emitted from the surface is considered to be 0–10 eV. The sample potential is −10 kV and the potential applied to the entrance grid is 0 V. A 50 gauss magnetic field is assigned to the system, with its direction parallel to the direction of the incoming positrons. The tilt angle θ is 45°. The trajectories show that the flight paths of the electrons and the positrons are clearly separated. Considering the distance between the entrance grid and the sample to be 10 mm, and the distance between the entrance grid and the electron detector to be 60 mm, the time spread induced by the 10-eV energy spread of the secondary electrons is only 51 psec in this calculation.

FIG. 3 Electronics

Figure 3:
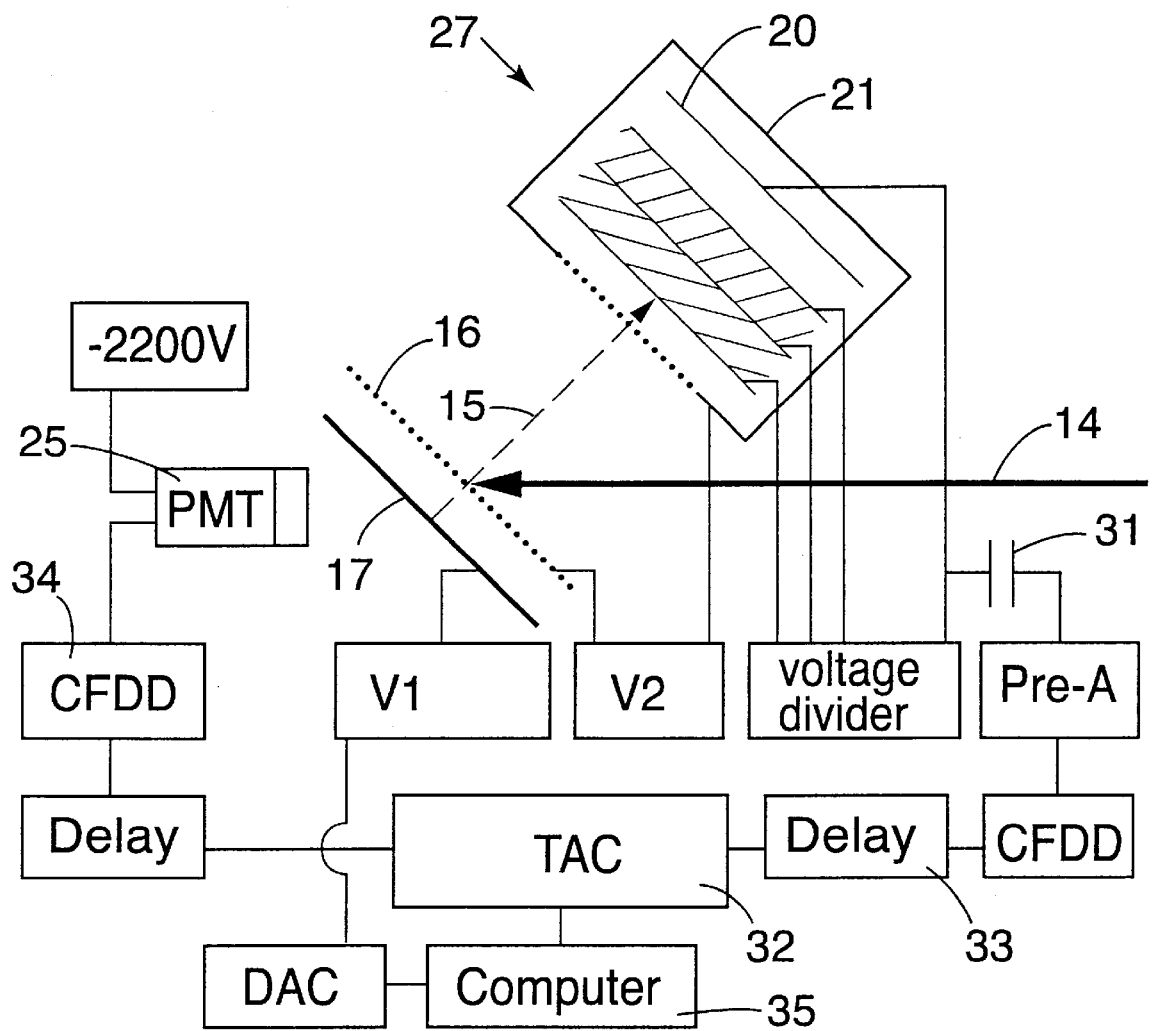
FIG. 3 is a block diagram of electronics that may be used with the positron lifetime spectrometer of this invention.

FIG. 3 is a block diagram illustrating a conventional delayed coincidence timing system that may be used with the DC beam positron lifetime spectrometer of this invention. The secondary electron signal is obtained through a capacitor 31 coupled to the MCP electron detector 20 and sent to the start input of time-amplitude-converter (TAC) 32. A time delay module 33 may be inserted between the MCP detector 20 and the TAC 32 if it is desired to use the electron signal as the stop signal. The gamma radiation signal from the PMT 25 is shaped by a constant fraction differential discriminator 34 and then sent to the stop input of the TAC 32. A computer 35 records and stores the number of events as a function of the difference between the start time and the stop time positron lifetime spectrum.

FIG. 4 Results

Figure 4:
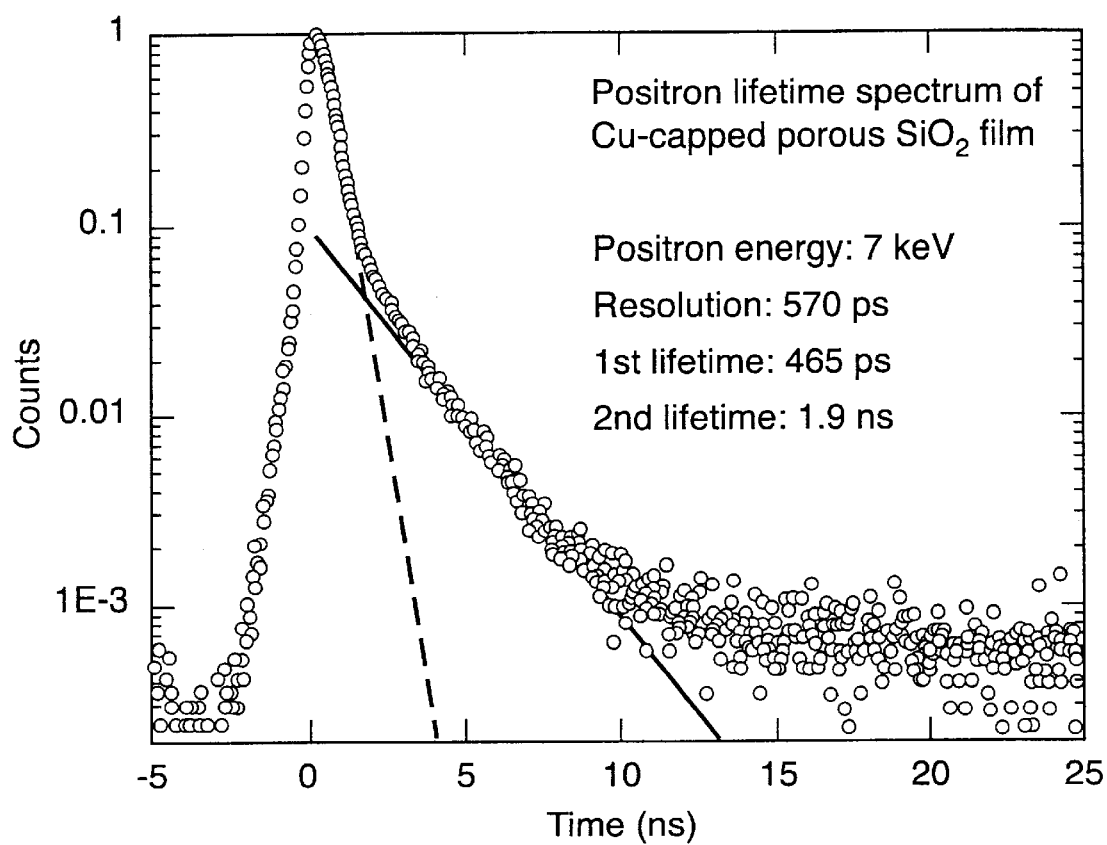
FIG. 4 is a typical positron lifetime spectrum of a Cu-capped porous $SiO_2$ film measured using the spectrometer. Two lifetime components are evident: 465 psec and 1.9 nsec, both shown as straight lines.

FIG. 4 is a representative positron lifetime spectrum of a Cu-capped porous $SiO_2$ film measured using the spectrometer of the present invention; The positron energy on the sample is 7 keV. The time resolution for the measured spectrum is 570 psec. Two lifetime components are observed: 465 psec and 1.9 nsec, shown as straight lines. A time range of 25 nsec is shown in FIG. 4. The remainder of the data, out to 300 nsec, is not shown in FIG. 4, but is completely without abnormal structures.

Positron backscattering, which can cause abnormal structures in some spectrometers, is not a problem in this invention because no ExB separator is used in front of the sample. The 570 psec or even higher time resolution is achieved by the elimination of most of the time spread induced by energy distribution of the secondary electrons. In the valid time range of this test of the invention (0–300 nsec), the signal-to-noise ratio was 3300.

While there has been shown and described what are at present considered the preferred embodiments of the invention, it will be obvious to those skilled in the art that various changes and modifications can be prepared therein without departing from the scope of the invention defined by the appended claims.

We claim:

1. A spectrometer for positron lifetime characterization studies, wherein a DC positron beam is directed onto a sample surface to produce annihilation gamma radiation and secondary electrons from the sample, the annihilation gamma radiation is detected by a gamma detector, and the secondary electrons are detected by an electron detector, comprising:

an entrance grid situated in the incident positron beam, said entrance grid positioned parallel to the sample surface, and said entrance grid arranged to have a higher electrical potential than the sample potential;

wherein:

the entrance face of the electron detector assembly is situated parallel to the entrance grid, the entrance face of the electron detector assembly is arranged to have the same potential as the entrance grid, and the sample surface, said entrance grid, and said entrance face of said electron detector assembly are disposed at a tilt angle to the incident DC positron beam.

2. The spectrometer of claim 1 wherein said tilt angle is such that the electron detector does not physically block the incoming positron beam.

3. The spectrometer of claim 1 wherein the secondary electrons generated by the bombardment of the primary positrons on the sample start the positron lifetime clock, and the detection signal of the annihilation gamma radiation of the positrons stops the positron lifetime clock.

4. The spectrometer of claim 1 further including a time delay that delays the secondary electron signal so that the detection signal of the annihilation gamma radiation of the positrons starts the positron lifetime clock, and the secondary electrons generated by bombardment of the primary positrons on the sample stops the positron lifetime clock.

* * * * *